US006012375A

United States Patent [19]

Eckstein

[11] Patent Number: 6,012,375

[45] Date of Patent: Jan. 11, 2000

[54] AIRCRAFT INFRARED GUIDED DEFENSE MISSILE SYSTEM

[76] Inventor: Donald B. Eckstein, 5123 Bradfield Dr., Annandale, Va. 22003

[21] Appl. No.: 08/226,546

[22] Filed: Apr. 12, 1994

Related U.S. Application Data

[63] Continuation-in-part of application No. 08/086,021, Jul. 6, 1993, abandoned.

[51] Int. Cl.[7] .................................. F41F 3/04; F41F 5/00

[52] U.S. Cl. .......................................... 89/1.816; 89/1.819

[58] Field of Search ............................... 89/1.816, 1.817, 89/1.818, 1.819

[56] References Cited

U.S. PATENT DOCUMENTS

| | | | |
|---|---|---|---|
| 3,456,552 | 7/1969 | Nash | 89/1.817 |
| 3,710,678 | 1/1973 | Abelin et al. | 89/1.816 |
| 3,988,961 | 11/1976 | Banta et al. | 89/1.816 |
| 4,412,475 | 11/1983 | Hornby | 89/1.816 |
| 5,058,481 | 10/1991 | Drummond et al. | 89/1.816 |

*Primary Examiner*—Theresa M. Wesson
*Attorney, Agent, or Firm*—Robert M. Downey, P.A.

[57] ABSTRACT

A defense missile system for an aircraft to provide protection against hostile attack on the aircraft, the system including an aerodynamically shaped launch housing structured for external mounting on the aircraft, and a missile assembly fitted within an interior launch chamber of the launch housing. The missile assembly includes at least one, and preferably several infrared guided missiles each contained within an elongate tube and having a propulsion engine at one end and a seeker head at the opposite end. A missile support structure holds each of the missiles within the launch chamber such that the missile seeker heads are at least partially exposed through an open aft end of the launch housing. A cylinder containing pressurized coolant gas is supported within the launch chamber and is interconnected to each of the missiles for providing coolant gas to the respective seeker heads. A missile fire activation system interconnects with a fire control located in the aircraft's cockpit which is electronically interconnected to each of the missiles to facilitate sequential release of the coolant gas and electrical power to each seeker head and subsequent firing of the missile, so as to effectively launch the missile in an aft direction relative to the aircraft. A drag inducing stage is provided for use with higher speed aircraft, such as fighter jets, including a tube fitted with a ballute which inflates when the tube is ejected from the launch chamber, effectively decelerating the forward speed of the tube so that the missile can be fired into the air stream with a positive aerodynamic stability in the rearward direction relative to the aircraft.

18 Claims, 4 Drawing Sheets

AIRCRAFT INFRARED GUIDED DEFENSE MISSILE SYSTEM

This application is a Continuation-In-Part application of U.S. patent application Ser. No. 08/086,021 filed on Jul. 6, 1993 now abandoned.

BACKGROUND OF THE INVENTION

1. Field of the Invention

The present invention relates to a missile system for an aircraft for launching a guided missile in order to intercept and destroy a hostile threat to the aircraft.

2. Description of the Related Art

While most military fighter and bomber aircraft are heavily equipped with offensive firepower for attacking enemy targets, including enemy aircraft, the need for defensive measures to protect the aircraft from attack is equally important. There are two basic threats to a military aircraft during a hostile encounter; those being gun projectiles (which are unguided or ballistic in nature once fired) and guided missiles. There are generally three types of guidance seekers which are employed on guided missiles for use against aircraft. The three types of guidance seekers include infrared, radar and laser. Infrared (IR) and radar make up approximately 98 percent of all deployed guidance seekers on surface-to-air or air-to-air missiles. Laser technology has only recently been used in missile seeker guidance systems and to date has only been deployed on short range surface-to-air missile systems. IR seekers guide on the heat generated by the intended target, while advanced IR seekers guide on the temperature differential between the intended target and its background. Ordinarily, the air frame of a moving target, such as a missile or aircraft, will become hot due to friction when moving at high subsonic or supersonic speeds. The IR seeker can detect this temperature differential between the target and the surrounding atmosphere. On the other hand, radar guided missiles guide on the radar energy that is reflected from the target aircraft.

As the missile seekers have become more capable and sophisticated, so have the electronic warfare (EW) measures used to counter them. Every modern fighter is equipped with a radar warning receiver which is tuned to frequencies commonly used by hostile radars and missiles. When an enemy radar has locked onto a friendly aircraft, the radar frequency modulation changes. This change is displayed to the pilot in the cockpit as a missile “lock”. The pilot then has to decide on a course of action to defend against this potential threat. The pilot can ignore the missile “lock”, try to disrupt or deceive the hostile missile’s guidance system by transmitting similar signals back to the missile, or the pilot can deploy bundles of chaff. Chaff is highly reflective to radar and creates an electronic “cloud” that may confuse or disrupt the missile’s guidance seeker. Chaff can be highly effective, but is only carried in limited quantities and is only effective for a short range and time period, since the deploying aircraft usually flies out of a protective area soon after deployment of the chaff.

IR guided missiles present several complications to a pilot who must defend against them. Since the IR seeker is passive in nature (i.e., it does not emit radio waves that can be detected by the fighter’s radar warning receiver), a pilot frequently does not know if one has been launched at him. Newly developed EW systems are able to warn a pilot of an IR guided missile’s approach either by use of a tail mounted radar or an IR sensor that detects the heat from the missile’s rocket motor. The primary problem which EW systems must be designed to overcome is the ability to correctly identify the type of threat seeker, either radar, IR, or laser, and then use specific types of counter-measures, either electronic techniques or expendables like chaff and flares. IR seekers can be decoyed away from the target aircraft by IR jammers that confuse the seeker. Alternatively, flares can be used which present a more intense heat source than the target aircraft, causing the missile to be diverted towards the flares and enabling the aircraft to maneuver away from danger. Electronic techniques are potentially effective, but require dedicated and expensive electronics. Expendables, such as chaff or flares, are fairly inexpensive, but must be carried in large numbers in order to be fully effective. Additionally, chaff and flares only work against one type of seeker, chaff being effective against radar and flares being effective against IR seekers. At this time, there is no identified EW or expendable technique that will detect and decoy laser guided missile seekers. Both electronic counter-measures (ECM) and expendables take up valuable aircraft volume which could otherwise be used for arsenal. Most importantly, ECM and expendables are both strictly defensive in nature and neither technology is capable of being used offensively to destroy hostile aircraft or missiles.

While IR guided missiles have been available since World War II, technical advances that allowed the missiles and guidance systems to be miniaturized have only recently become available. Because of these recent developments, two classes of IR missiles have evolved. The first was designed to be mounted on aircraft to engage other aircraft. The Sidewinder is the most common of this type used on aircraft. The U.S. version of this type weighs approximately 150 pounds, is 5–6 inches in diameter and is about 5 feet long with large fixed control fins and wings. The second type of IR missile is man-portable and is primarily used by soldiers to engage hostile aircraft. The Stinger is the most common of this type. The U.S. version weighs approximately 40 pounds in its launch tube, is 3–4 inches in diameter and is about 3 feet long with collapsible control fins/wings. The primary effective difference between these two types of missiles is performance. The Sidewinder carries a much larger warhead, has 2–3 times more range, flies at higher speeds and has the energy to make very high g turns. Both missiles are very capable of downing virtually any aircraft.

While both the Sidewinder and Stinger missiles are highly effective for their intended purpose, which is essentially offensive in nature, there still exists a need for a defensive-type missile system for use on an aircraft to defend against hostile threats, including enemy aircraft or missiles fired at the aircraft.

SUMMARY OF THE INVENTION

The present invention is directed to a defensive guided missile system for use on an aircraft, and primarily a military type aircraft, for the purpose of destroying hostile threats to the friendly aircraft, including enemy aircraft and missiles fired at the friendly aircraft.

The defense system includes a launch housing preferably having an aerodynamically shaped forward end and an at least partially open aft end exposing an interior launch chamber within the launch housing. Mounting means are provided to facilitate mounting of the launch housing to any one of various hard points of the aircraft such that the open aft end is oriented in an aft or rearward direction relative to the aircraft. The launch housing may be a dedicated pod or may be incorporated as part of an external fuel tank which may be carried under the wings or fuselage, depending on the type of aircraft.

The defense system further includes a missile assembly which is structured and disposed for attachment within the launch chamber of the launch housing. The missile assembly includes at least one infrared guided missile, and preferably a plurality of missiles, each having an IR seeker head at one end and propulsion means at an opposite end. It is contemplated that the stinger type missile, or a derivative form thereof, would be ideal for use with the missile assembly of the present invention. Each missile is contained within an elongate tube, the tubes being attached to and supported by a missile support structure fitted within the launch housing. The support structure is specifically designed to hold each of the missile tubes, supporting the missiles in spaced apart, generally parallel relation with the respective seeker heads of each missile protruding from the open aft end of the launch housing.

A flask or cylinder for containing pressurized coolant gas is supported within the launch chamber and interconnected to each of the missiles for supplying coolant gas to the respective seeker heads as demanded by the user. The coolant gas makes the IR seeker more sensitive to heat, thereby enabling the seeker head to detect an approaching hostile threat. The IR seeker head may either detect heat generated from a hostile missile's engine or a temperature differential between a hostile missile's air frame and the surrounding atmosphere. An enemy aircraft can be detected by the IR seeker in the same manner.

A missile fire control means is interconnected to the missile assembly for activating the IR seeker head and the propulsion unit of the missile so as to facilitate launching of the missile from the launch housing. The missile fire control means interconnects with a missile actuation control within the cockpit of the aircraft which may be in the form of a trigger type control, wherein movement of the trigger to a first position releases the coolant gas and electrical power to the seeker head of one of the missiles in sequence, enabling the seeker system of the missile. Once a target (enemy aircraft or missile) is detected and the seeker locks on to the target, the trigger would be moved to a second position to activate the propulsion unit causing the missile to be launched.

The present EW systems used on military aircraft must first correctly determine the type of seeker of the hostile missile before any counter-measures can be deployed. Once the hostile missile is properly identified, the present EW systems will only deceive or confuse the hostile missile, not destroy it. The present invention solves both of these problems. Once an aircraft's EW system has identified that a hostile missile or aircraft is tracking his aircraft, the pilot can activate the defense system of the present invention in order to launch a stinger type missile to counter the hostile threat without ever having to determine how the hostile threat is guided. Due to the hostile missile's hot booster rocket motor and high speed (which significantly heats the missile's air frame), it will present a hot, high contrast target for the IR seeker head to lock onto. While the type of missile used in the present invention generally flies at subsonic speeds, it will intercept a target flying directly toward it at a high speed. This intercept profile will significantly shorten the time to intercept. The resulting Mach 1–Mach 3 engagement will also maximize the kinetic energy transfer of the defense missile's warhead. A near miss that does not destroy the threat would undoubtedly disable it and prevent a successful attack. Should the engagement of the present invention's defense missile be unsuccessful, the pilot still has time to take further defensive actions which might include chaff, flares, maneuvering, etc.

The performance of this system can be further enhanced by installing a gimbled seeker head on the missile. The gimbled seeker head is standard on larger IR guided air to air missiles such as the Sidewinder, Magic and the Python. A gimbled seeker head would significantly increase the potential launch window (both horizontally and vertically) and decrease reaction time (i.e., from threat warning to launch), especially for larger transport size aircraft such as C-130's, C-141's and the like. Any reduction in range caused by launching the missile at a large off-boresite angle would be more than compensated for by the reduced system response time.

When using the system of the present invention on higher speed aircraft, such as fighter jets, the "forward" velocity of the missile needs to be substantially reduced so that the missile can enter the air stream with a positive aerodynamic stability, traveling in the "rearward" direction relative to the aircraft. In order to decelerate the "forward" airspeed of the missile, it is necessary to introduce drag to the missile assembly prior to launching the missile into the air stream. The present invention accomplishes this by incorporating a ballute (a type of inflatable parachute) on a ballute tube which contains the missile therein. The ballute tube, containing the missile, is received within the missile tube in the launch chamber. The ballute is attached to and folded around the ballute tube when contained within the launch chamber. A small gas cartridge ejects the ballute tube (ballute stage) from the missile tube at the initiation of the firing sequence. Upon ejection and entering the air stream, the ballute inflates, rapidly decelerating the ballute stage to the desired "forward" airspeed, preferably between 80–120 knots. When the ballute stage reaches the desired missile ejection airspeed (this can be determined by use of an airspeed sensor or a G meter that senses the G conditions of ejection, ballute inflation and stabilized forward flight), the first stage of the missile motor is ignited, ejecting the missile from within the ballute tube. The missile then enters the air stream with positive aerodynamic stability, after which a sustainer motor of the propulsion means is ignited.

While the system of the present invention is primarily defensive in nature, it could also be easily used in an offensive capacity. For instance, a fighter pilot using the defense missile system of the present invention would not have to point his nose towards an adversary to take a shot. A hostile aircraft which closes in on the "six o'clock" position of an aircraft using the system of the present invention is directly exposing itself to being shot in the face. Additionally, a fighter pilot who misses with a head-on missile shot during a high speed merge with an enemy aircraft could immediately take a shot with a missile of the defense missile system when the enemy aircraft turns to reengage. Obviously, the system of the present invention would significantly increase the number of offensive missile shots available to a fighter pilot. Since the system allows large numbers of relatively inexpensive missiles to be carried by an aircraft, the pilot would be more at ease taking a lower percentage shot than they ordinarily would with the more expensive Sidewinder, Sparrow or Amraam missiles.

With the foregoing in mind it is a primary object of the present invention to provide a defense missile system for an aircraft capable of detecting and destroying hostile threats, such as enemy aircraft and missiles.

It is another object of the present invention to provide a defense missile system for an aircraft which is specifically structured to launch an infrared guided missile from an aircraft in an aft direction to effectively destroy a hostile threat, such as an enemy aircraft or missile approaching the friendly aircraft.

It is a further object of the present invention to provide a defense missile system which can be easily and relatively inexpensively adapted for use on existing military aircraft to protect against hostile threats, such as enemy aircraft and missiles.

It is still a further object of the present invention to provide a defense missile system which is adapted to use relatively inexpensive infrared guided missiles, such as the Stinger missile, enabling the system to use a large number of IR guided missiles for use in defending the aircraft from hostile threats.

It is yet a further object of the present invention to provide a defense missile system which can be incorporated with an external fuel tank to be mounted under the wings or fuselage of an aircraft so as not to limit the offensive ordinance which is normally carried by a military aircraft.

It is still an object of the present invention to provide a defense missile system for a military type aircraft which is both defensive in nature and offensive in nature.

It is still a further object of the present invention to provide a defense missile system which is adapted for use on high speed tactical aircraft which travel at speeds in the range of 400–800 knots, wherein the system is provided with a drag inducing stage so that the missile can enter the air stream with a positive aerodynamic stability, when fired in a rearward direction relative to the aircraft These and other objects of the present invention will be more readily apparent in the description which follows.

BRIEF DESCRIPTION OF THE DRAWINGS

For a full understanding of the nature of the present invention reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
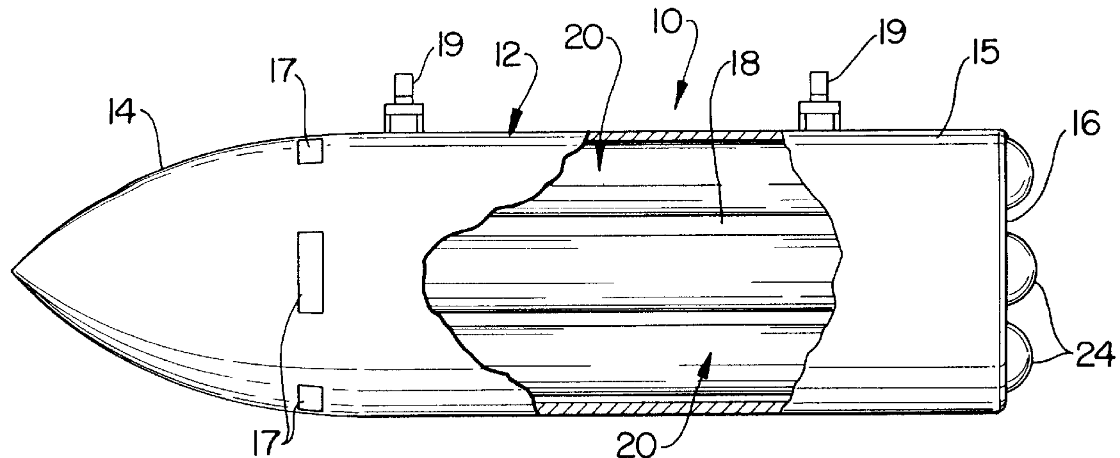
FIG. 1 is a side plan view, in partial cutaway, illustrating the defense missile system of the present invention.
Figure 2:
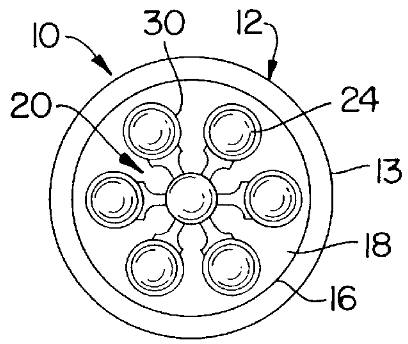
FIG. 2 is an aft end view of the defense system of the present invention illustrating positioning of the missile assembly within an interior launch chamber of the launch housing.

As shown throughout the several views of the drawing, the present invention is directed to an aircraft defense guided missile system, generally indicated as 10, for use primarily on a military aircraft. Referring initially to FIGS. 1 and 2, the defense missile system 10 includes a launch housing 12 having a generally aerodynamically shaped outer shell 13 including a conical forward nose portion 14, a side wall section 15 and an open aft end 16. The open aft end 16 exposes an interior launch chamber 18 within the launch housing 12 which is specifically structured and configured for receipt of a missile assembly 20 therein. The missile assembly 20 includes a plurality of guided missiles 22 which are supported within the launch housing 12 such that a seeker head 24 of each of the missiles 22 is exposed through the open aft end 16. At least one vent port 17 is provided in the side wall 15 of the launch housing 12 to permit ventilation of exhaust from the missile's 22 rocket motors when launched. The launch housing 12 further includes several pylon mounting lugs 19 to facilitate fixed external mounting of the launch housing 12 to one and possibly several hard points of the aircraft in the same general manner in which external fuel tanks are commonly mounted to military aircraft. With this in mind, the purpose of the vent ports 17 can better be appreciated. Obviously, the vent port 17 will substantially relieve any sheering force exerted on the mounting lugs 19 caused by the thrust of the missile's rocket motors during launching from within the launch chamber 18.

Figure 3:
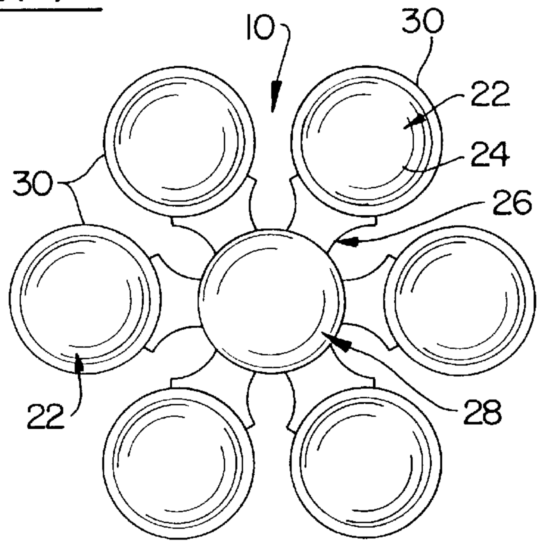
FIG. 3 is an aft end view of the missile assembly of the present invention.

As shown in FIG. 3, the missile assembly 20 includes several missiles 22 which are supported in spaced apart parallel relation by a missile support structure 26. A coolant gas storage cylinder 28 is also supported by the missile support structure 26, being preferably centrally positioned relative to the surrounding missiles 22 and the launch chamber 18, as shown in FIG. 2. The cylinder 28 is adapted to contain pressurized coolant gas such as argon gas, to be supplied to the seeker heads 24 of the missiles upon demand.

The missiles 22 are each individually contained within an elongate missile tube 30 which extends substantially the length of the missile 22, allowing the seeker head 24 to protrude through one open end 31 thereof. The missile tube 30 is provided with end caps 32, 33 to cover opposite open ends during transport. Upon inserting the missile assembly 20 within the launch chamber 18, the end caps 32, 33 would ordinarily be removed, exposing the seeker heads 24 of each of the missiles 22 through the open aft end 16 of the launch housing 12. In a preferred embodiment, each of the missiles 22 is provided with a two-stage solid propellant rocket motor. The two-stage rocket motor includes a first ejector motor 36 for providing sufficient thrust to launch the missile clear of the launch housing 12. A second stage 38 provides sufficient thrust to propel the missile 22 at speeds up to Mach 2 over a maximum range of approximately 8000 meters. The missile tube 30 is further provided with electrical contacts 40 for interconnection of a missile fire control system thereto. A gas coolant supply fitting 42 is further provided on the missile tube 30, and includes a check valve to facilitate one directional supply of coolant gas to the seeker head 24 upon demand.

Figure 5:
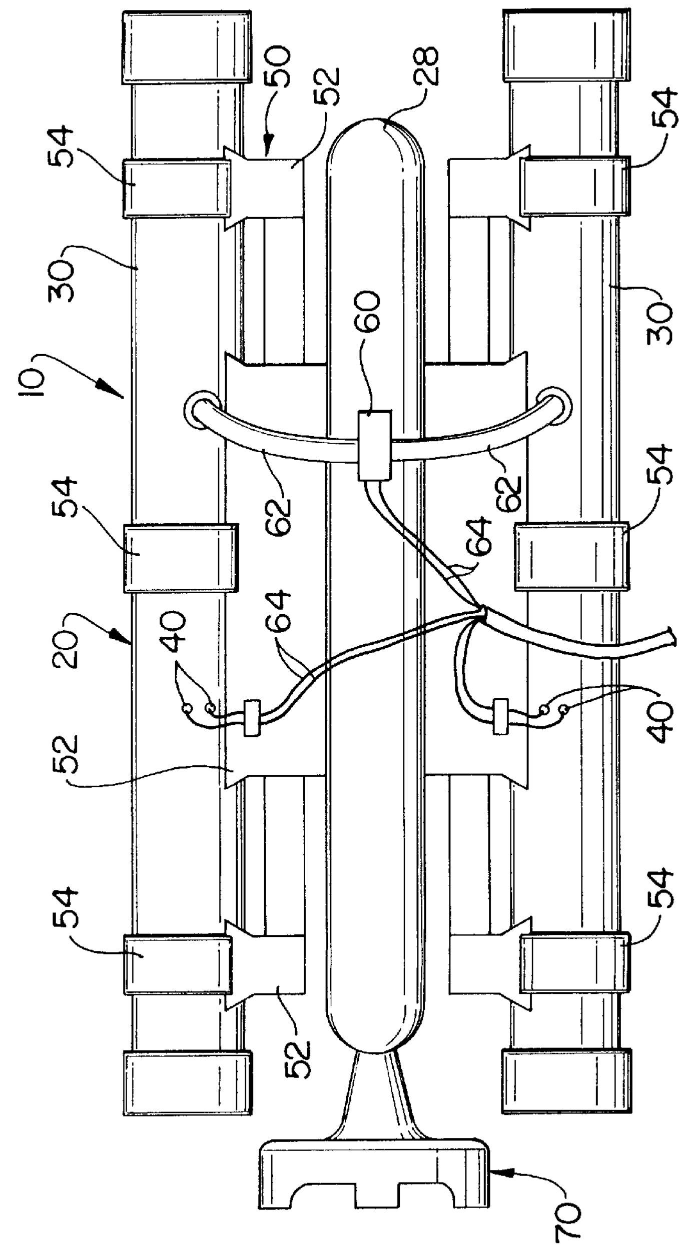
FIG. 5 is a partial top plan view of the missile assembly illustrating support of the missiles on the missile support structure and interconnection of the missiles with a coolant gas storage cylinder.

The missile assembly 20 is best illustrated in FIG. 5, wherein the missile tubes 30 are each individually supported by brackets 50 of the missile support structure 26. Each of the brackets 50 includes a plurality of bracket arms 52 structured and disposed to support the missile tube 30 at various points along its length. The bracket arms 52 are each provided with a securing strap 54 which wraps about the missile tube 30 securing the missile tube 30 to the bracket arms 52 of the respective bracket 50. The gas coolant storage cylinder 28 is centrally supported by the missile support structure 26 within the missile assembly 20 so as to better facilitate interconnection of the cylinder 28 to each of the missiles 22. In a preferred embodiment, a directional valve 60 is provided and interconnected to the gas storage cylinder 28 for directing flow of the coolant gas to each of the seeker heads, in sequence, prior to launching of the respective missile 22. A coolant gas supply conduit 62 interconnects between the directional valve 60 and the supply port 42 of the missile tube 30, thereby enabling pressurized cooling gas to be delivered to the seeker head 24. The fire control system is electrically interconnected by various conductors 64 to the directional valve 60 and the electrical contacts 40 on each missile tube to facilitate activation of a respective one of the missiles 22 for firing. The electrical conductors 64 lead to a fire control mechanism in the cockpit of the aircraft for controlled actuation of the respective missiles 22. The missile support structure 26 may further be provided with an attachment structure 70 to facilitate releasable attachment of the missile assembly 20 within the launching chamber 18.

Figure 6:
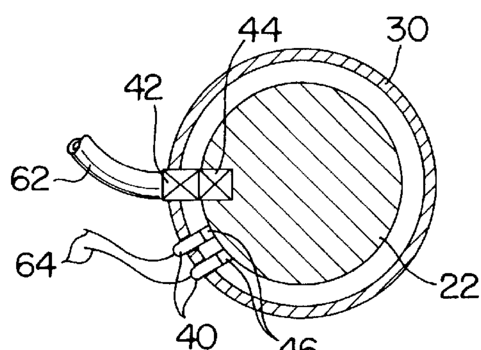
FIG. 6 is a sectional view of the missile contained within the sealed tube, illustrating the electrical connection of the firing control with the missile and the coolant gas supply means.

Interconnection of the gas coolant supply and firing control system to the missile is best illustrated in FIG. 6. The gas coolant supply conduit 62 leads to the supply port 42 on the missile tube 30. A check valve 44 is provided on the missile to facilitate one directional flow of the coolant gas to the missile 22. Upon firing of the missile 22, the supply port 42 would release from the check valve 44, preventing escape of the coolant gas from the seeker head 24 of the missile 22. The missile fire control is further electrically interconnected to slipper-type electrical contacts 40 on the missile tube 30 and corresponding slipper contacts 46 on the missile 22. The electrical contacts 40 and 46 frictionally engage one another while the missile 22 is contained within the missile tube 30. Upon firing of the missile 22, the contacts 40 and 46 separate without obstructing ejection of the missile 22 from the tube 30.

Figure 7:
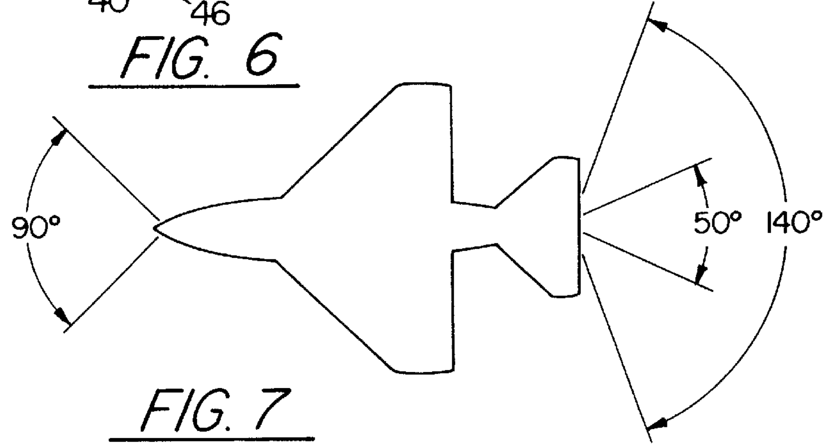
FIG. 7 is a top plan view of an aircraft illustrating a "field of view" of the missile seeker heads as expanded by a variation in directional heading of the aircraft.
Figure 4:
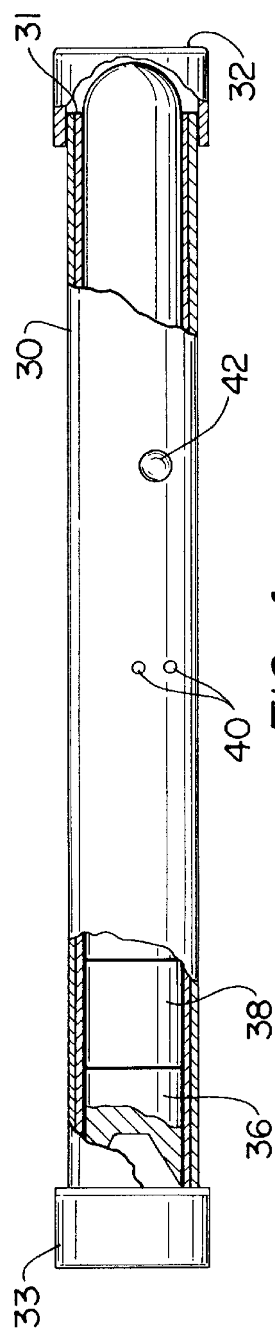
FIG. 4 is a side plan view of a missile, contained in a sealed tube as used in the system of the present invention.

In use, the defense missile system of the present invention would ordinarily be activated by the pilot once the aircraft's electronic warfare system identifies an enemy aircraft or missile tracking the pilot's aircraft. At this point, the pilot would initiate activation of one of the missiles 22 causing the coolant gas and electrical power to be directed to the seeker head 24 of one of the missiles. The activated missile 22 would then begin to detect the differentials in temperature or hot spots, which would most likely be the hostile threat pursuing the aircraft. As shown in FIG. 7, the normal field of view of a gimbled seeker head is approximately 50 degrees. However, it is a common tactic for the pilot to vary the aircraft's course heading by up to 90 degrees to maximize the installed radar's and pilot's field of view. By varying the aircraft's heading by up to 90 degrees, the effective field of view of the seeker head 24 would be expanded to 140 degrees (see FIG. 7), thus enabling the seeker head 24 to detect virtually any hostile threat approaching from behind the aircraft.

Figure 8:
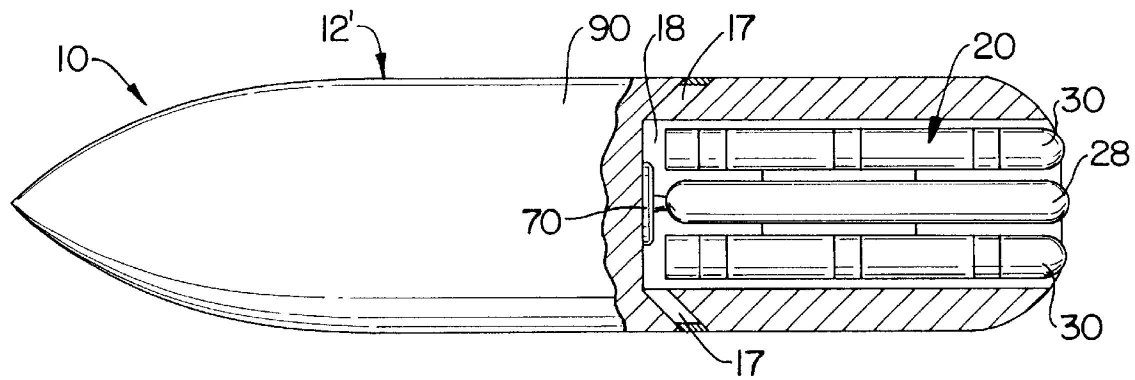
FIG. 8 is a top plan view in partial section of a fuel tank and missile assembly of the system of the system of the present invention.
Figure 9:
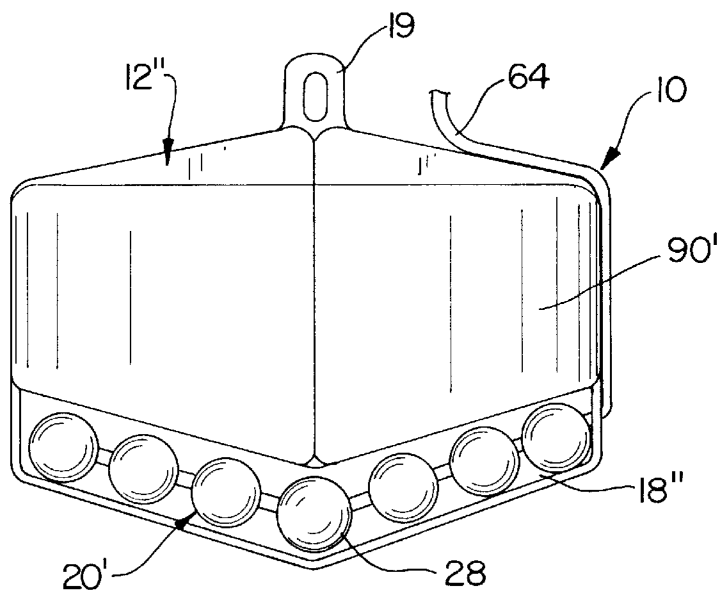
FIG. 9 is an aft end view of still another embodiment of the system of the present invention.

Referring to FIGS. 8 and 9, alternative embodiments of the present invention are shown in which the missile assembly 20 is integrated with a fuel tank 90. FIG. 8 illustrates one embodiment wherein the launch chamber 18 would be disposed in an aft section of the launch housing 12', with a remainder of the housing 12' having a sufficient fuel storage capacity for extended flight time. FIG. 9 illustrates another alternative embodiment of a center line type housing 12" similar to the external fuel storage tank used on the F-16 fighter. In this embodiment, the modified version of the missile assembly 20' is disposed within a launch chamber 18" below the fuel storage tank 90. As with all of the embodiments, the missiles 22 would protrude from an open aft end of the launch housing 12", for launching in an aft direction relative to the directional heading of the aircraft. Both the embodiments of FIGS. 8 and 9 effectively combine the defense missile system of the present invention with an external fuel tank as commonly required by most fighter aircraft for extended flight time. Due to the fact that the missile assembly 20 is relatively light in weight, the load exerted on the aircraft would be essentially the same as that normally exerted by an external fuel tank. Accordingly, the embodiments of FIGS. 8 and 9 would preserve the amount of offensive ordinance ordinarily carried by a fighter aircraft during combat.

Figure 10:
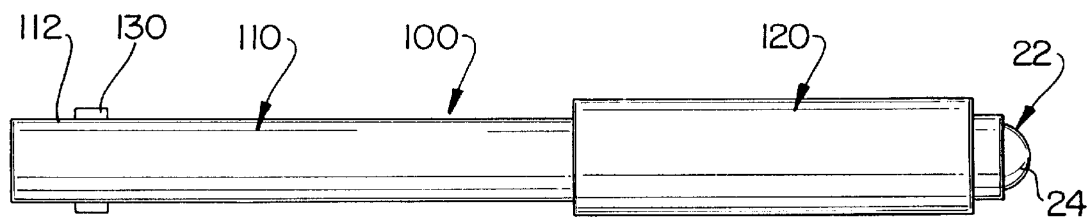
FIG. 10 is a side plan view of a ballute stage of the present invention, including a ballute tube and attached ballute shown folded around the ballute tube for containment within the missile tube in the launch chamber.
Figure 11:
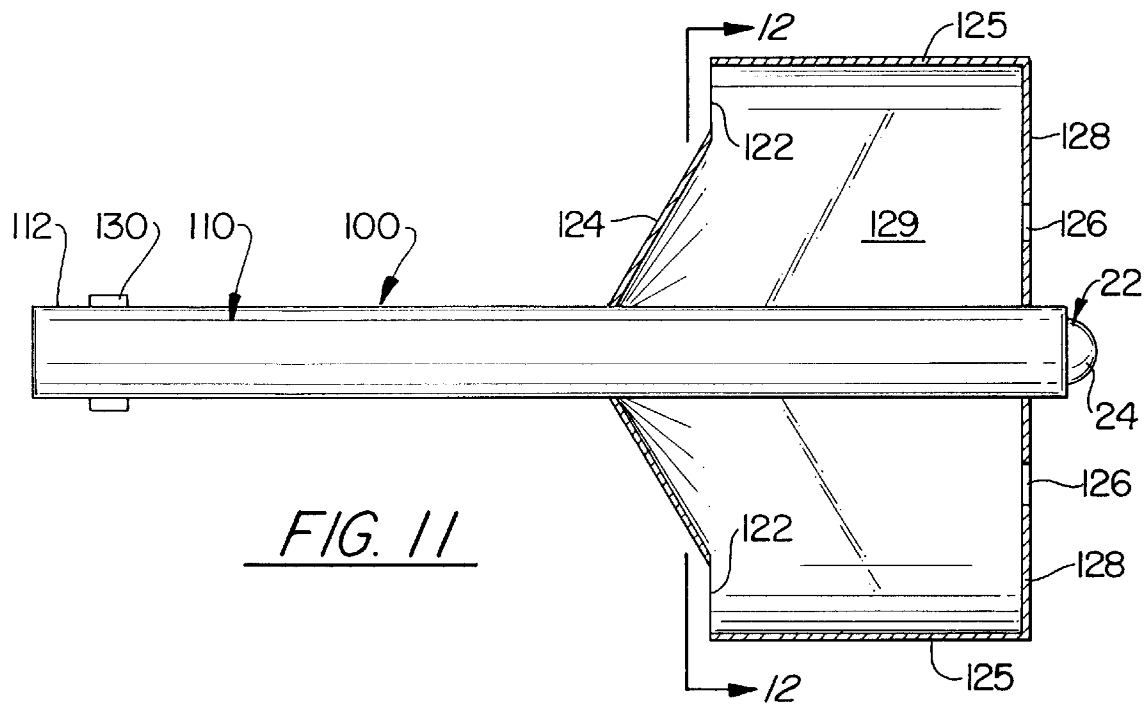
FIG. 11 is a side plan view in partial section, illustrating the ballute in an inflated position after the ballute stage has been ejected into the air stream.
Figure 12:
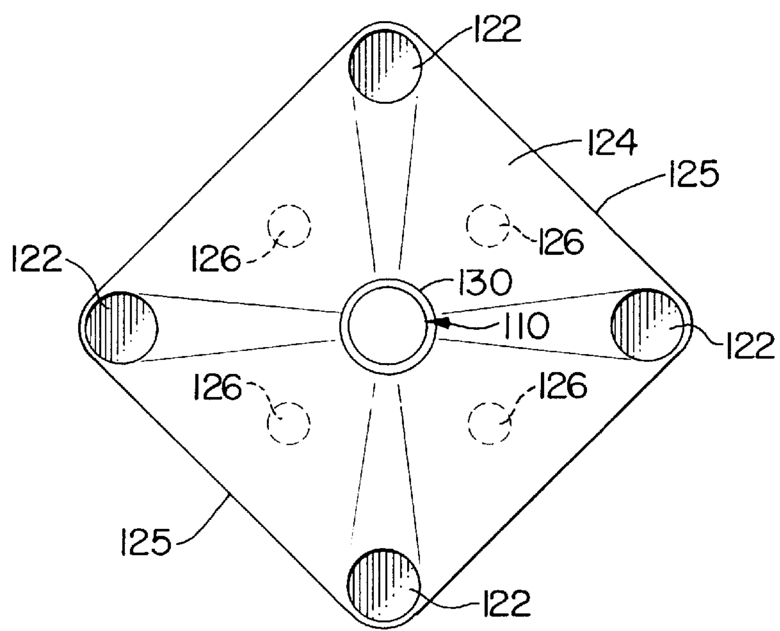
FIG. 12 is a front end view of the inflated ballute taken along the line 12—12 of FIG. 11.

In order to introduce drag to the missile assembly so that the missile 22 can enter the air stream with a positive aerodynamic stability when launched from a high speed aircraft, such as a fighter jet, an additional ballute stage 100 is provided, as seen in FIGS. 10–12, including a ballute tube 110 which is adapted to be received within the missile tube 30, the ballute tube 110 containing the missile 22 therein. The ballute stage 100 further includes a ballute 120 which is attached to and folds around the ballute tube 110 so that the entire ballute stage 100 can be received within the missile tube 30 for ejection therefrom. A small gas cartridge (not shown for purposes of clarity) ejects the ballute stage 100 at the initiation of the firing sequence. A spacer element 130 at an opposite end 112 of the ballute tube provides stability to the ballute tube 110, preventing wobbling of the ballute tube 110 as it is ejected from the missile tube 30. Upon ejection and entering into the air stream, the ballute 120 inflates, as seen in FIG. 11, rapidly decelerating the ballute stage 100 to a desired "forward", airspeed, preferably between 80–120 knots. The inflated ballute is specifically structured to avoid interference with the seeker head's 24 field of view prior to ignition of the missiles first stage 36. The ballute is preferably made of a fabric material, similar to parachute material and includes four equally spaced air intakes 122 on a forward end 124 thereof. A side wall structure 125 extends between the forward end 124 and a rear end 128. The air intakes 122 are specifically designed and positioned to permit airflow to pass therethrough as the ballute stage 100 is subjected to the air stream, once ejected from the missile tube 30. As air from the air stream passes through the intakes 122, the ballute inflates, keeping the ballute 120 symmetrical and the ballute stage 100 (including the missile) stable during high speed releases. Small exhaust holes 126 on the rear 128 of the ballute help to maintain even inflation and stability of the ballute 120, permitting air to vent from within an interior chamber 129 of the ballute at a slower rate than that of the airflow entering the intakes 122. The ballute is designed to create a specific amount of drag so as to reduce the velocity of the ballute stage to a predetermined forward airspeed, at which point, the missile 22 can be fired in the rearward direction. In this manner, the missile 22 would always experience the same aerodynamic conditions when ejected from the ballute tube 100 (regardless of the launching aircraft's airspeed and angle of attack). When the ballute stage reaches the desired missile ejection airspeed, the first stage of the rocket motor 36 is ignited, ejecting the missile 22 from within the ballute tube 110. The missile 22 then enters the air stream with positive aerodynamic stability, at which point the sustainer rocket motor second stage 38 is ignited. The entire process of ejecting the ballute stage 100, ballute inflation and stabilization, and missile ejection and rocket motor ignition takes approximately 2–4 seconds depending upon the particular airspeed of the launching aircraft.

Now that the invention has been described,

What is claimed is:

1. A defense system for an aircraft of the type including a plurality of hard points adapted for mounting of external loads thereto, said defense system including:

a launch housing having an aerodynamically shaped forward end and an at least partially open aft end disposed in communication with an interior cavity defining a launch chamber, a missile assembly structured and disposed for attachment to said launch housing within said launch chamber and including:

at least one infrared guided missile having a seeker head at one end and propulsion means at an opposite end, gas coolant storage means for storing pressurized gas coolant therein, gas coolant supply means interconnected between said gas coolant storage means and said missile for supplying gas coolant to said seeker head upon activation thereof, connection means for connecting said missile assembly to said launch housing within said launch chamber, missile fire control means electrically interconnected to said missile assembly for activating said seeker head and said propulsion means to facilitate launching of said missile from said launch housing, and mounting means for mounting said launch housing to one of the hard points of the aircraft with said aft end of said launch housing oriented in an aft facing direction relative to the aircraft so as to cause said missile to be launched in a direction substantially opposite to the directional heading of the aircraft.

2. A system as recited in claim 1 wherein said launch housing includes at least one vent port in a side wall thereof, said vent port being structured and disposed to direct exhaust gas from said propulsion means of said missile during launching thereof.

3. A system as recited in claim 2 wherein said launch housing includes a plurality of said vent ports disposed in spaced relation about said side wall of said launch housing.

4. A system as recited in claim 3 wherein said missile assembly includes a plurality of missiles, each of said missiles independently connected to said gas coolant storage means.

5. A system as recited in claim 4 wherein each of said missiles are contained within an elongate missile tube.

6. A system as recited in claim 5 wherein said gas coolant supply means is independently interconnected to each of said missiles and said gas coolant storage means.

7. A system as recited in claim 6 wherein said missile assembly further includes a missile support structure being structured and disposed to support each of said missile tubes, and missiles contained therein, in spaced relation from said gas coolant storage means, said launch housing and a remainder of said missile tubes.

8. A system as recited in claim 7 wherein said missile support structure includes a plurality of spaced apart bracket sets, each of said bracket sets being structured to support a corresponding missile tube in substantially longitudinally extending relation within said missile chamber such that said seeker head is at least partially exposed through an open end of said missile tube and said open aft end of said launch housing.

9. A system as recited in claim 8 wherein each of said bracket sets includes a plurality of locking bands adapted to be secured in spaced relation from one another about said missile tube, said locking band being structured and disposed to maintain said missile tubes within said bracket sets.

10. A system as recited in claim 1 wherein said mounting means includes a plurality of pylon mounting lugs on an outer surface of said launch housing, said pylon mounting lugs including an aperture therethrough to accommodate a standard bombrack mounting shackle.

11. A system as recited in claim 1 wherein said launch housing includes an aircraft fuel storage tank therein, in segregated relation to said launch chamber.

12. A system as recited in claim 11 wherein said aircraft fuel storage tank is disposed within a forward portion of said launch housing.

13. A system as recited in claim 11 wherein said aircraft fuel storage tank is disposed above said launch chamber.

14. A system as recited in claim 1 further including drag inducing means for reducing a relative forward velocity of said infrared guided missile prior to launching thereof into a surrounding air stream.

15. A system as recited in claim 14 wherein said drag inducing means includes a ballute stage including a ballute tube sized and configured to receive said missile therein, said ballute stage further including an inflatable ballute attached to an exterior of said ballute tube and structured to inflate upon ejection of said ballute stage from within said launch housing so as to decelerate a forward airspeed of said ballute stage and said missile contained therein relative to the aircraft.

16. A system as recited in claim 15 wherein said ballute is formed of a fabric material and includes a forward end, a rear end, and a surrounding wall structure extending between said forward and said rearward end in surrounding relation to an interior chamber thereof.

17. A system as recited in claim 16 wherein said ballute further includes a plurality of air intake ports on said forward end structured to permit airflow to pass therethrough and into said interior chamber so as to inflate said ballute from a folded, collapsed position about said ballute tube to an inflated position.

18. A system as recited in claim 17 wherein said ballute further includes a plurality of exhaust holes on said rear end thereof for permitting air to escape from within said interior chamber at a slower rate than a rate of airflow entering through said air intake ports.

* * * * *